(12) United States Patent
Zanelli (10) Patent No.: US 6,515,657 B1
(45) Date of Patent: Feb. 4, 2003

(54) ULTRASONIC IMAGER

(76) Inventor: Claudio I. Zanelli, 2100 Prospect St., Menlo Park, CA (US) 94025

( * ) Notice: Subject to any disclaimer, the term of this patent is extended or adjusted under 35 U.S.C. 154(b) by 0 days.

(21) Appl. No.: 09/502,722

(22) Filed: Feb. 11, 2000

(51) Int. Cl.$^7$ .............................................. G06T 15/00
(52) U.S. Cl. ...................................................... 345/419
(58) Field of Search ................................ 345/424, 630, 345/631, 632, 633, 634, 419; 600/411

(56) References Cited

U.S. PATENT DOCUMENTS

| | | | |
|---|---|---|---|
| 4,173,228 A | 11/1979 | Van Steenwyk et al. .... | 128/653 |
| 4,581,636 A | 4/1986 | Blaker et al. ................ | 358/112 |
| 4,596,145 A | 6/1986 | Smith et al. ................... | 73/626 |
| 5,181,514 A | 1/1993 | Solomon et al. ....... | 128/660.09 |
| 5,226,113 A | 7/1993 | Cline et al. ................. | 395/124 |
| 5,295,486 A | 3/1994 | Wollschläger et al. . | 128/661.01 |
| 5,329,929 A | 7/1994 | Sato et al. ............. | 128/660.65 |
| 5,343,865 A | 9/1994 | Gardineer et al. ..... | 128/662.05 |
| 5,425,370 A | 6/1995 | Vilkomerson .......... | 128/662.06 |
| 5,515,853 A | 5/1996 | Smith et al. ........... | 128/661.01 |
| 5,515,856 A | 5/1996 | Olstad et al. .......... | 128/661.04 |
| 5,546,807 A | 8/1996 | Oxaal et al. ................... | 73/606 |
| 5,577,502 A | 11/1996 | Darrow et al. ........... | 128/653.1 |
| 5,582,173 A | 12/1996 | Li .......................... | 128/660.07 |
| 5,630,417 A | 5/1997 | Petersen et al. ........ | 128/660.08 |
| 5,720,291 A | 2/1998 | Schwartz ................. | 128/661.1 |
| 5,771,895 A | 6/1998 | Slager .................... | 128/662.06 |
| 5,797,849 A | 8/1998 | Vesely et al. ............... | 600/461 |
| 5,817,022 A | 10/1998 | Vesely ......................... | 600/443 |
| 5,865,750 A | 2/1999 | Hatfield et al. ............. | 600/443 |
| 5,868,673 A | 2/1999 | Vesely ........................ | 600/407 |
| 5,876,342 A | 3/1999 | Chen et al. ................. | 600/443 |
| 5,899,863 A | 5/1999 | Hatfield et al. ............. | 600/443 |
| 5,916,168 A | 6/1999 | Pedersen et al. ............ | 600/443 |
| 6,016,439 A * | 1/2000 | Acker ........................ | 600/411 |

OTHER PUBLICATIONS

Berg, S.; Torp, H., "Volumetric Blood Flow Estimation Using Dynamic Three–dimensional Ultrasound Color Flow Imaging", *1998 IEEE Ultrasonics Symposium. Proceedings*, (Cat. No. 98CH36102), Part vol. 2, (Oct. 1998) pp. 1513–1516 vol. 2.

Brody, Herb, "Venturing Out", *Benchmarks, Technology Review*, (Nov.–Dec. 1999) p. 33.

(List continued on next page.)

*Primary Examiner*—Phu Nguyen
(74) *Attorney, Agent, or Firm*—James F. Feeney; Shirley L. Church (57) ABSTRACT

An ultrasound imaging system superimposes sectional views created from volumetric ultrasound data and the location data for an intervention device, such as a catheter. The position of an interventional medical device may be shown, in one or more views, relative to organs and tissues within a body as the interventional device is moved. The interventional device positional data is updated continuously and is superimposed on tissue images that may be updated less frequently, resulting in real-time or near real-time images of the interventional device relative to the tissues.

The superimposed images permits medical personnel to perform procedures such as angiograms with minimal or no exposure of patients to x-rays and contrasting dye. The look and feel of the familiar fluoroscopy-like imaging may be maintained, or a three dimensional real-time, or near real-time projected image of the intervention medical device relative to an organ or tissue may be provided.

44 Claims, 4 Drawing Sheets

OTHER PUBLICATIONS

Duann, J.-R.; Lin, S.-B.; Hu, W.-C.; Su, J.-L, "Computer System for Four–dimensional Transesophageal Echocardiographic Image Reconstruction", *1999 Elsevier Science Ltd.; Computerized* Medical Imaging and Graphics, vol. 23, No. 4, (Jul.–Aug. 1999) pp. 173–179.

Gilja, O.H.; Hausken, T.; Berstad, A.; Odegaard, S., "Measurements of Organ Volume by Ultrasonography"; *Proceedings of the Institution of Mechanical Engineers, Part H (Journal of Engineering in Medicine)*, vol. 213, No. H3 (1999) pp. 247–259.

Oshiro, O.; Matani, A.; Chihara, K.; Mikami, T.; Kitabatake, A., "Three Dimensional Echocardiography with a Reconstructed B–Mode Image", *Japanese Journal of Applied Physics, Part 1 (Regular Papers, Short Notes& Review Papers)*, vol. 36, No. 5B, (May 1997) pp. 3221–3225.

Oshiro, O.; Matani, A.; Chihara, K., "3D Dynamic Echocardiography with a Digitizer", *Japanese Journal of Applied Physics, Part 1 (Regular Papers, Short Notes & Review Papers )* vol. 37, No. 5B, (May 1998) pp. 3097–4100.

Oshiro, O.; Nambu, M.; Chihara, K., "3D Echocardiography Using a 3D Positioner", *Proceedings of the 20th Annual International Conference of the IEEE Engineering in Medicine and Biology Society. vol. 20 Biomedical Engineering Towards the Year 2000 and Beyond* , (Cat. No. 98CH36286) Part vol. 2 (Oct.–Nov. 1998) pp. 783–784 vol. 2.

Oshiro, O.; Nambu, M.; Matani, A.; Chihara, K., "3D Heart Imaging System Using Echocardiogram and a Digitizer for a US Probe Location", *Medical Imaging Technology,* vol. 17, No. 2, (Mar. 1999) pp. 165–171.

Rees, M., "Cardiac Imaging: Present Status and Future Trends", *British Journal of Radiology,* vol. 70, Special Issue, (1997) pp. S162–167.

Schmauder, M.; Orglmeister, R.; Aldekamp, F.; Gross, C.M.; Waigand, J., "Computer–assisted Analysis of Intravascular Ultrasound Records for Three–dimensional Reconstruction of Coronary Vessel Walls", *Zeitschrift fur Medizinische Physik,* No. 1 (1999) pp. 22–29.

Wahle, A.; Prause, G.P.M.; DeJong, S.C.; Sonka, M., "Geometrically Correct 3–D Reconstruction of Intravascular Ultrasound Images by Fusion with Biplane Angiography—Methods and Validation", *IEEE Transactions on Medical Imaging,* vol. 18, No. 8, (Aug. 1999) pp. 686–699.

* cited by examiner

ULTRASONIC IMAGER

BACKGROUND OF THE INVENTION

1. Field of the Invention

The present invention relates to ultrasonic imaging. More particularly, the present invention relates to creating sectional views from volumetric ultrasound data and superimposing positional data for an interventional device, such as a catheter.

2. Background of the Invention

Many medical procedures involve inserting a catheter, or other interventional device, into a patient for a variety of purposes. One such procedure is cardiac catheterization for an angiogram.

To observe the condition of blood vessels within the heart, radio-opaque dye is injected into the bloodstream through the catheter and an x-ray image is taken. Typically, this procedure involves inserting a catheter into an artery in the patient's groin area and guiding the catheter through the arterial system and the aorta to the heart. In order to position the catheter and monitor its location within the patient, one or more x-ray images may be taken prior to injecting dye for the angiogram.

A catheter may be directly visible in an x-ray image, however, a heart typically is not. In order to determine the location of the catheter relative to the heart, dye may be injected through the catheter into the bloodstream. The dye acts as a contrasting agent allowing the heart to be located, by imaging the dye flowing through it. The image of the heart is then "frozen" at a point in time when the dye location (and concentration), provides the best image. Often, this snapshot image of the heart is traced on a transparent overlay which is then superimposed on a display monitor. After the dye concentration decreases, the overlay may be used to track the catheter location and movements relative to the heart, as indicated by the overlay. There are two disadvantages to this process. First, the image of the heart, made visible with the dye, is only temporary, requiring the overlay to track the catheter movement. Second, if the patient's position changes, the heart imaging must be repeated.

In addition to locating a catheter relative to a heart for an angiogram, there are many other medical procedures where an interventional device is inserted into a patient. In most, if not all, such procedures, locating and positioning the interventional device within a patient is extremely important.

Figure 1:
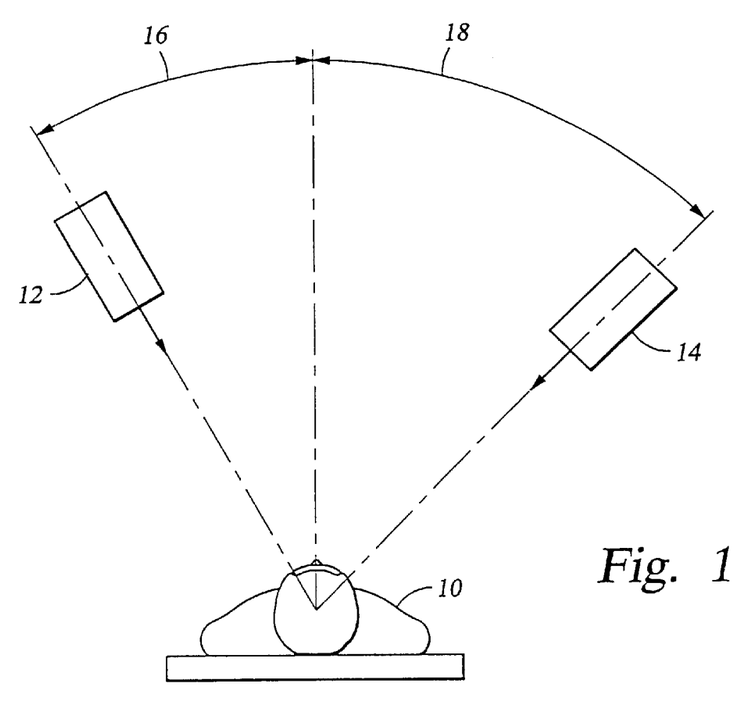
FIG. 1 is a schematic sectional depiction of a patient and x-ray equipment.

Multiple views, or x-ray orientations, of a patient are often desirable to visualize objects and locations in three dimensions. Although there are many possible combinations of such views, some are favored by medical personnel for particular procedures. For cardiac imaging, the right anterior oblique (RAO) and the left anterior oblique (LAO) views are common. FIG. 1 shows a schematic sectional depiction of a prone patient 10 and x-ray sources 12 and 14. The RAO and LAO views are taken from the patient's right and left, respectively, of the anterior (front) of the heart. The oblique angle, shown as angles 16 and 18, is the measure of how far off the vertical an x-ray source is oriented. The multiple views are often taken with a single x-ray source that is repositioned between positions 12 and 14. An imaging system that readily presents RAO and LAO views allows medical personnel to view images in a familiar format, as this is what is presently standard in the art. Multiple preferred views for other procedures might similarly be predefined.

There are problems with present practices. First, x-rays and fluoroscopy produce radiation, and the effect of this radiation over the long term may be harmful. This is especially true for the medical personnel subjected to repeated radiation exposures over the course of an entire career.

In addition, the radio-opaque dye may harm the patient. For example, an angiogram is often performed on patients with serious heart problems. Injecting chemicals that may cause sensitivity, or an allergic reaction, directly into the heart of such a patient may cause a serious problem, and there is the possibility of kidney damage from the dye.

Finally, x-ray techniques require complex x-ray equipment and the costly overhead associated with such equipment. While this may not be a primary concern in a well equipped modern hospital, it is of concern in less developed or remote locations.

Ultrasound based imaging methods offer some potential advantages over x-ray based imaging methods. Ultrasound methods do not expose the patient or medical personnel to radiation and may reduce or eliminate the need for costly x-ray equipment. Also, the ability of ultrasound methods to directly image soft tissue and blood vessels, without the need for radio-opaque dye as a contrasting agent, eliminates the potential dye-related harms to a patient.

It would be desirable to have an imaging system that could eliminate, or serve as a partial substitution for, x-ray and fluoroscopy methods of imaging in procedures such as angiography and tissue biopsies. Preferably, such a system would present medical personnel with multiple views that are displayed simultaneously.

U.S. Pat. No. 4,173,228, issued to Steenwyk and Childress on Nov. 6, 1979, describes a catheter locating device ("the '228 patent"). The '228 patent uses an induction coil adjacent to the catheter tip, and a remote sensing device to monitor the amplitude and phase of signals induced in the coil, as a means of detecting the catheter location. However, an electrical signal from an induction coil is not well suited for detection by ultrasound imaging equipment. The '228 patent does teach one technique for locating a catheter, but it lacks the ability to directly map that location to a 3-D ultrasonic image of tissues within the body. Instead, such a device determines a catheter location relative to a position on the skin surface and a depth estimate, based on the magnitude of the signal received at the skin surface. It would be desirable to locate the catheter relative to internal body tissues, not the skin.

U.S. Pat. No. 5,515,853, issued to Smith, et al. on May 14, 1996, describes a 3-D ultrasound tracking system based on triangulation ("the '853 patent"). Using a network of at least four piezoelectric transducers exchanging signals, and an integrated personal computer (PC) as a digital controller, the '853 patent accurately measures the relative distances between the transducers. However, like the '228 patent discussed above, an apparatus based on the '853 patent lacks the ability to map the location of a catheter to a 3-D ultrasonic image of tissue within the body. Instead, the reference frame for catheter location information is the location of other piezoelectric transducers. For example, a series of transducers contained in a chest harness around a patient may be used to triangulate the position and orientation of a catheter relative to the chest harness, by measuring the distances to transducers mounted in the catheter. The '853 patent does briefly mention the possibility of "overlaying" transducer location information on a video loop, created from x-rays or ultrasound, to facilitate visualization of the catheter location. However, there is no teaching of how this overlay process might be performed. In contrast, an embodiment of the present invention is directed to describing the catheter location relative to tissue within the body in one or more 2-D views.

U.S. Pat. Nos. 5,817,022 and 5,868,673, ("the '022 and '673 patents") issued to Vesely on Oct. 6, 1998, and on Feb. 9, 1999, respectively, are both, continuations-in-part from the application that became the '853 patent. Both also claim 3-D ultrasound tracking of interventional medical instruments by triangulating between a transducer attached to the medical instrument and a network of transducers either inside a patient's body or on the body surface. It would be desirable to simplify the apparatus so that a network of transducers is not required.

The '022 patent locates a medical instrument relative to the network of transducers in 3-D, and then displays a 2-D ultrasound image within the 3-D coordinate system. The '022 patent describes an "imaging modality system", that may acquire 2-D, 3-D or 4-D image data, an "image registration system" to register the position the [medical] instrument within the image data and a "user interface" to perform a desired function, such as selecting a particular view for display. However, there are no detailed descriptions of these elements, or teachings which would permit one of ordinary skill in the art to create a system combining such elements.

The '673 patent describes a system for performing surgery while tracking the location of a medical device relative to a network of transducers, on or within the body. The medical device location is then mapped to the network of transceivers, but not directly to any portion of the body tissue.

Ultrasound image data for an object, such as a heart, consists of the "echodensity" sampled at multiple locations within an object. This echodensity can be thought of as somewhat equivalent to the color or intensity of a visual image. The echodensity is a function of the sound velocity within the tissue, as well as the tissue density. Although a 3-D image of echodensity, with continuous gradations along three dimensions, may lack the clarity of the sharp edges in a solid model, the gradations contain a significant amount of information about the tissue. A solid modeling approach to presenting a 3-D ultrasound image typically uses a threshold value. That is, all echodensity values are divided into two bins, those above and those below the threshold. Values above the threshold are opaque and those below are transparent. This threshold technique adds clarity to the wide variations of the "murky" echodensity data, by distinguishing solid features within the data, at the expense of the detail stored in those many values.

TomTec Imaging Systems, formerly of Boulder, Colo., now TomTec Imaging Systems GmbH of Munich, Germany, produced a video tape describing a 3-D ultrasound imaging system ("the TomTec system"). TomTec Imaging systems, Clinical Three-Dimensional Echocardiography, VHS/NTSC, 19:20, 040-012.0, 07-96 (video tape). The TomTec system creates a 3-D cardiac image, with the use of an ultrasound transducer in the form of an endoscope, and produces an image of the surfaces of the heart, essentially a solid model. That is, the surface of the heart is displayed without any information about the internal muscle tissue. The TomTec system does not appear to have been commercially successful.

SUMMARY OF THE INVENTION

The ultrasound imaging system of the present invention superimposes sectional views created from volumetric ultrasound data and the location data for an intervention device, such as, but not limited to, a catheter. The position of catheter may be shown, in one or more views, relative to organs and tissues within a body as the catheter is moved. The catheter positional data is updated continuously and is superimposed on tissue images that may be updated less frequently, resulting in real-time or near real-time images of the catheter relative to the tissues.

The superimposed images allow medical personnel to perform procedures such as angiograms with minimal exposure of patients to x-rays and contrasting dye. However, the look and feel of the familiar fluoroscopy-like imaging may be maintained.

DETAILED DESCRIPTION

The present invention is directed at superimposing an image of an interventional medical device, such as a catheter, and a three-dimensional (3-D) ultrasound image of an organ or tissues, such as a heart, and creating one or more projections from the superimposed image data. The two sets of image data may be updated at the same or different frequencies. The image of the medical device may be updated more frequently to show its current location, as the device is guided or repositioned within a patient by medical personnel. The projections made from the superimposed images preferably reflect the current location of the medical device, and depending on the frequency of updating the image of the organ or tissues, may also show a real-time image of such organ or tissues.

The present invention may be used with a wide variety of interventional medical devices, such as, but not limited to, catheters, probes, cannulas, stylets, and needles, and is not intended to be limited to use with any particular interventional medical device. For convenience, this disclosure will use the term catheter, instead of the more generic term intervention medical device, since the example description is related to use of the apparatus and method of the invention in cardiac procedure; however, this is not meant to imply any limitation on the scope of the invention.

The present invention may be used in connection with ultrasound images of any organ, portion of an organ, or group of organs, and the present invention is not intended to be limited to any particular image subject matter. There are situations in which it may be desirable to use the present invention in conjunction with x-ray methods. For example, if an ultrasound transducer is positioned so that only locations in the vicinity of the heart can be imaged, x-ray methods might be used to track a catheter from its insertion point near the groin until it comes into view with the transducer.

The present invention may also be used with "4-D ultrasound images". That is, repetitive sequences of 3-D images in time, such as, but not limited to, images of a heart beating as it goes through one or more cycles. The 4-D ultrasound images may be depicted and displayed as repetitive sequences of images, or cine loops. Alternatively, a single point in the time sequence may be selected, effectively transforming the 4-D image into a 3-D image. Preferably, the present invention allows updates of the catheter location at a frequency independent of the repetitive sequence frequency and the frequency of individual image frames within the sequence. This disclosure will use the term "dynamic display" when 4-D image data is distinguished from 3-D image data. Otherwise, the term "image data" may apply to either 3-D or 4-D image data.

The output of the present invention is one or more projections created from the superimposed image data. Although the projections are typically displayed on one or more cathode ray tube (CRT) monitors, the present invention may output the projections to any type of graphic display device(s), such as a thin film transitor flat screen display, or to a graphic output file for storage or further image processing. The present invention is not intended to be limited to use with any particular type of graphic display device or output file format. Multiple projections, typically taken from differing orientations with respect to the image data, are often beneficial in visualizing locations in a 3-D space. An embodiment of the present invention uses two standard views, right anterior oblique (RAO) and left anterior oblique (LAO) as "default" projection orientations.

As the trend towards faster computer processors continues, eventually the present invention will allow for real-time or near real-time updates of projections created from 3-D image data. At present, the acquisition of image data, and the projection processing discussed below, takes too long for such real-time updates. Given the current constraint on computing power, the present invention is preferably used in an environment where the patient is immobilized. This permits use of a single set of image data which may be used continuously while a catheter is moved relative to the patent and the image data.

For purposes of the examples described below, references to a dynamic display embodiment of the present invention, presumes that the position of the organs and tissue return to the same position and orientation within a patient at the end of each repetitive sequence, or cycle. That is, the cycle may consist of "local" movement but no "global" movement relative to the immobilized patient is anticipated. In contrast, movement of the catheter is anticipated, so the location of the catheter is updated frequently, preferably in real-time. The updated catheter location is then superimposed on the relatively static organ or tissue image data before the projections are created.

Collecting 3-D ultrasound image data, while certainly not a trivial procedure, is known to those of skill in the art, and is not intended to be an element of the present invention. Rather, the present invention uses such data, however collected, as input. U.S. Pat. No. 5,181,514, issued to Solomon, et al. on Jan. 26, 1993, describes a transesophageal echo cardiography transducer device which may be used to collect 3-D ultrasonic image data ("the '514 patent"). This device, with a rotatable ultrasound transducer array, may be inserted into a patient's esophagus and positioned adjacent to the heart. A motor and drive mechanism, which remains external to the patient, is used to control the probe with the transducer array and obtain 3-D image data. A transesophageal transducer, such as described in the '514 patent, might be used to collect cardiac image data. As the present invention is not limited to any particular method or apparatus for collecting image data, it is intended that as advances are made in ultrasound data collection, the present invention may utilize such improved image data as input.

Image data will preferably take the form of the 3-D array:

$I(x,y,z)$

Or, in the case of image data for a dynamic display, in the form of the 4-D array:

$I(x,y,z,t)$

Where I represents the echodensity, or "intensity," of the ultrasound image at a point defined by the 3-D Cartesian coordinates x, y and z. The particular choice of orientation for the x, y and z axes does not effect the present invention. Preferably, the axis orientation is used consistently. For a dynamic display, t refers to the instant in time representing when the echodensity data was sampled within the repetitive sequence. Image data may be collected in different formats, or coordinate systems, and then converted to the preferred format using transformation formulae known to those of ordinary skill in the art.

In one embodiment of the present invention the I values at each sampled point in space will be binary representations of the echodensity values. The values may be in either integer or floating point format. Although integer values are typically better suited to efficient mathematical algorithms, this efficiency may be effectively lost if numerical interpolation methods using floating point values are selected for integration. The need for numerical interpolation and integration will be further explained below. The I values, for monochromatic embodiments of the present invention, will preferably map to a specific gray scale value that will be used to display the image. For example, eight bit integer I values may represent 256 gray scale values, from 0 to 255. Floating point I values may be grouped in ranges, each of which corresponds to a gray scale resolution of the display. The range of gray scale resolution values chosen will depend on both the characteristics of the display (where higher resolution produces better images) and the processing speed of the image processing device (where higher resolutions require more calculations per pixel). Gray scales for displaying images are known to those of ordinary skill in the art. The present invention is not intended to be limited to any particular gray scale resolution.

In addition to the number of gray scale values, or gray scale resolution, the spatial resolution of the input image data also effects both the quality of the display and the number of calculations required. That is, image data sampled at many points in 3-D space will generally produce a better image than the same object sampled at fewer points. The trade off being that the additional image sample points may require more calculations, which typically requires a more complex and rapid handling system or slows the image processing.

Although techniques for collecting the ultrasound image data are not within the scope of the present invention, and image data is treated as input to the present invention, an embodiment of the present invention does allow a user to call for an update of image data as needed. For example, if the medical personnel detect that a patient has shifted, changing the relative position of the object being imaged and the catheter, new I(x, y, z) values may be collected. In another embodiment of the present invention, a patient movement that is more than a pre-defined threshold amount may trigger a call for updating the image data. As long as there is little or no relative movement between the object being imaged and the catheter, there is no need to update the image data. Preferably, the catheter is located using the same apparatus used to collect the 3-D ultrasound image data, I(x, y, z). The format of the catheter location data will depend somewhat on the type of catheter used, as well as the associated means of locating the catheter.

The catheter location may correspond to the direct echodensity data depicting the image of the catheter, including any image enhancements from active catheter devices such as a vibration mechanism. U.S. Pat. No. 5,343,865, issued to Gardineer and Vilkomerson on Sep. 6, 1994, describes a catheter vibrating mechanism ("the '865 patent"). A vibrating mechanism, such as described in the '865 patent, may enhance the visibility of a catheter, or other interventional medical device, that are attached to it in an ultrasound imaging system. The present invention is preferably used with such an active catheter. Potential benefits include faster imaging of the location, a clearer image, and such an active catheter reduces the required sensitivity for the imaging system. The present invention is not, however, intended to be limited to use with an active catheter, or any particular type of active catheter system. The image of the catheter location may also be enhanced, for better visibility, through techniques such as brightening, increasing the contrast, or enlarging the catheter image before superimposing the catheter location data and the 3-D image data. With some embodiments of the present invention, a false image, or icon, may be used in place of the catheter image data. Such techniques will be further described below. It is very important, however, that the catheter location be matched closely to the coordinate system of the image data.

Figure 2:
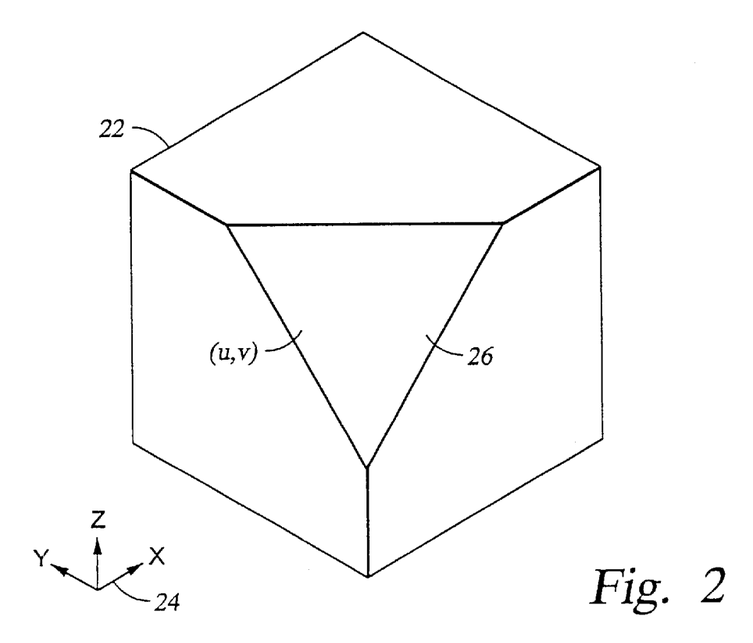
FIG. 2 is a diagram of a 3-D image space in accordance with an embodiment of the present invention.

In order to create projections of the 3-D image data, one or more projection planes must be defined. FIG. 2 depicts a 3-D space or volume 22. Volume 22 is the portion of space containing the imaged objects, such as organs within a patient's body cavity, and could take virtually any 3-D shape. Volume 22 uses (global) axes 24 to define a Cartesian coordinate system for orientation and measurement. A 2-D plane 26 is selected relative to volume 22, with (local) axes denoted as (u, v). Typically, plane 26 is defined by a unit vector $\hat{n}$, normal to (u, v). Unit vector $\hat{n}$ can be defined as:

$$\hat{n} = (n_1 \hat{x} + n_2 \hat{y} + n_3 \hat{z})$$
$$= (n_1, n_2, n_3)$$

and, because $\hat{n}$ is a unit vector:

$$1 = \sqrt{n_1^2 + n_2^2 + n_3^2}$$

Where $\hat{x}$, $\hat{y}$ and $\hat{z}$ are unit vectors along the x, y and z axes, respectively, and ($n_1$, $n_2$, $n_3$) are the direction cosines of $\hat{n}$. Those of ordinary skill in the art will recognize that there are many mathematically equivalent ways of defining plane 26 and its normal vector $\hat{n}$.

Imposing the condition:

$$\hat{u} \perp \hat{z}$$

the directions of unit sectors $\hat{u}$ and $\hat{v}$ can be defined, using the constant R, as;

$$\hat{u} = R(-n_2, n_1, 0)$$

where;

$$R = \frac{1}{\sqrt{n_1^2 + n_2^2}}$$

and;

$$\hat{v} = R(-n_1 n_3, -n_2 n_3, n_1^2 + n_2^2)$$

The construction of the projection on plane 26, can be calculated by performing the integration:

$$P(u, v) = \int_{\vec{x}} I(x, y, z) dS$$

That is, the image data, I(x, y, z), is summed along the line $\vec{x}$ onto P(u, v), where the vector $\vec{x}$ is an integrating line parallel to $\hat{n}$ and is defined by the equation:

$$\vec{x} = \vec{x}_0 + S \hat{n}$$

The starting point, $\vec{x}_0$, is given by:

$$\vec{x}_0 = u\hat{u} + v\hat{v}$$
$$= Ru(-n_2, n_1, 0) + Rv(-n_1, n_3, -n_2 n_3, n_1^2 + n_2^2)$$
$$= R(-un_2 - vn_1 n_3, un_1 - vn_2 n_3, v(n_1^2 + n_2^2))$$

and, $$S = k\sigma$$

where k is an integer and $\sigma$ is the integration interval used for the numerical implementation.

S can be thought of as the thickness, or depth, of the image data used to create P(u, v). In some embodiments of the present invention S, and the starting point $\vec{x}_0$, are set such that the projection is created from only a relatively thin slice of the image data I(x, y, z). Preferably, the depth of the image data used in projection plane 6 is defined by the user along an axis parallel to $\hat{n}$.

Figure 3:
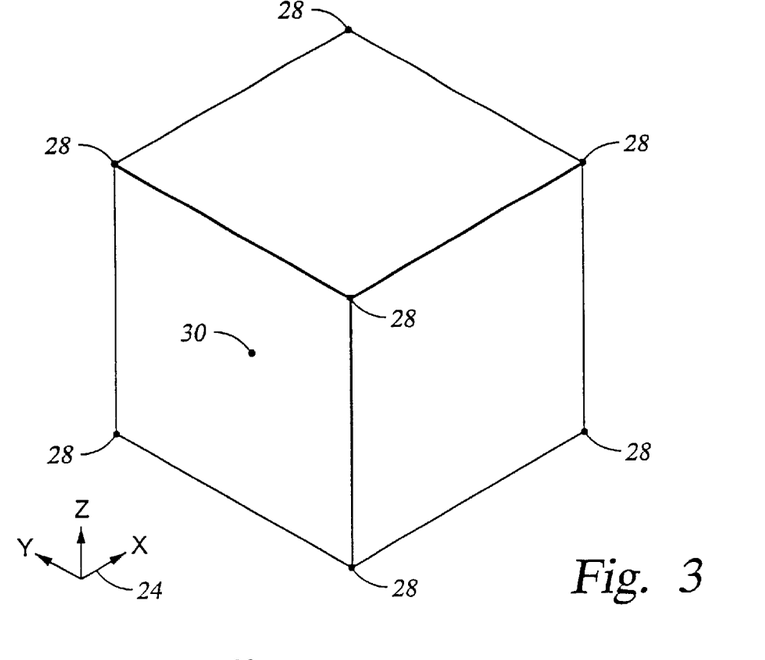
FIG. 3 is a schematic diagram of point location among regularly spaced image data samples in accordance with an embodiment of the present invention.

The numerical implementation of the integration used to calculate P(u, v) may require interpolation. That is, the vector $\vec{x}$ and integration interval $\sigma$ may result in locations that do not directly coincide with any data sample locations in I(x, y, z). Referring now to FIG. 3, which depicts a set of image data values 28, corresponding to image sample locations within I(x, y, z). Values 28 are shown, for clarity, as regularly spaced in three dimensions, although the same principals apply for irregularly spaced image values. Location 30 is a point along $\vec{x}$ used in the calculation of P(u, v), that does not correspond to the location of any value 28. Those of ordinary skill in the art will recognize that there are many techniques available for assigning a data value to location 30. A few of these techniques are, in increasing order of complexity, matching the value of the "nearest neighbor", averaging nearby values and computing weighted averages. The present invention, however, is not intended to be limited to any particular interpolation technique.

U.S. Pat. No. 5,226,113, issued to Cline, et al. on Jul. 6, 1993, describes using reverse ray casting to project volumetric images unto an image plane rotated at any arbitrary angle ("the '113 patent"). The present invention takes 3-D volumetric image-data, as one input, and projects 3-D image data onto one or more image planes, which may be rotated relative to the axes of the 3-D image data. The present invention may use the projection techniques of the '113 patent, or any other technique, and is not intended to be limited to any particular method of projecting 3-D image data to create a 2-D view in an image plane. U.S. Pat. No. 5,865,750, issued to Hatfield, et al. on Feb. 2, 1999, also described using reverse ray casting to project volumetric images ("the '750 patent"). Like the '113 patent, the technique described by the '750 patent may be used by an embodiment of the present invention to project 3-D image data.

The above projection creation procedure may be repeated for each desired projection display. An embodiment of the present invention allows the user to select a first projection, corresponding to either an RAO or a LAO orientation, at a user selected number of degrees off the vertical, with a second projection (default) orientation corresponding to the other. Preferably, defining the direction of the second projection orientation would require very little input from the user, and instead would use translations from the first projection orientation to orient the second.

Presenting projections to medical personnel in a familiar format, such as RAO and LAO orientations, is merely one capability of the present invention. Unlike x-ray images taken from only one or two orientations, the 3-D image data I(x, y, z) used with the present invention may create virtually any view(s) a user might select. For example, a projection could be created of the tissue in front of a catheter, as viewed along the axis of the catheter.

Figure 4:
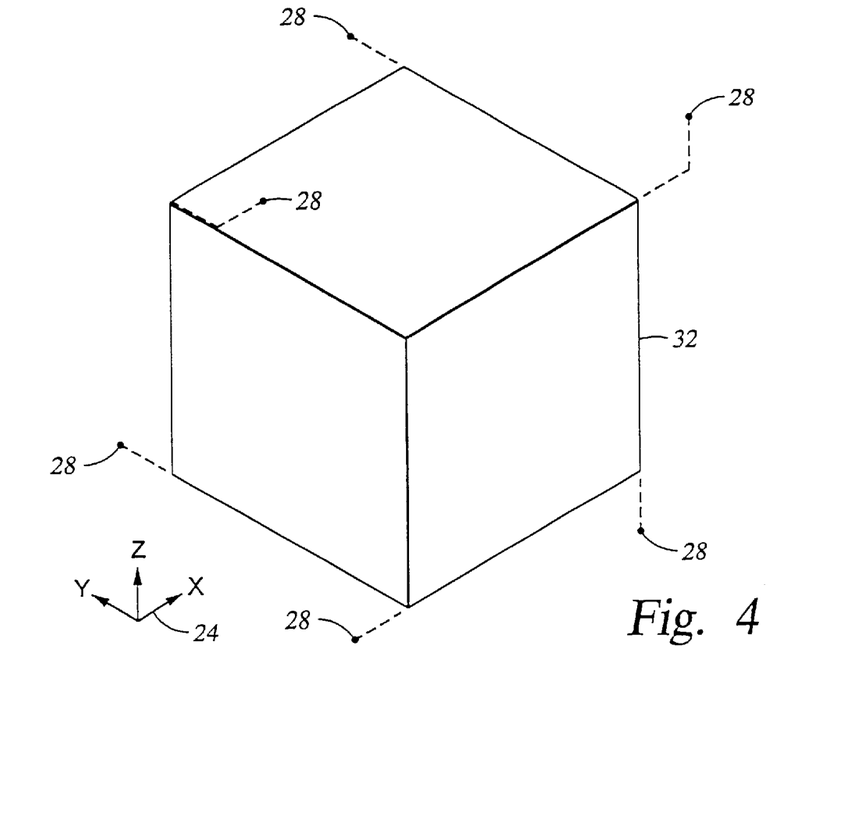
FIG. 4 is a schematic diagram of irregularly spaced image data samples in accordance with an embodiment of the present invention.

The simplest form for the image data, is equally spaced image samples in each of the x, y and z directions. Unequally spaced, or irregularly spaced, samples may also be used with the present invention although the calculations may become more complex, and time consuming. Irregularly spaced samples may also be pre-processed and converted to equally spaced image samples, by any one of a variety of techniques, for use by an embodiment of the present invention. An embodiment of the present invention may pre-process irregularly spaced I(x, y, z) data values. Referring now to FIG. 4, which depicts an irregularly spaced set of image data values 28, relative to a regular spacing location template 32. Data values 28 may be used to interpolate, or create, data samples on template 32. Similar to the interpolation discussed above, the present invention is not intended to be limited to any particular method interpolating or translating data values 28. Some projection algorithms may benefit from such a pre-processing of irregular image data into regularly spaced locations.

Figure 5:
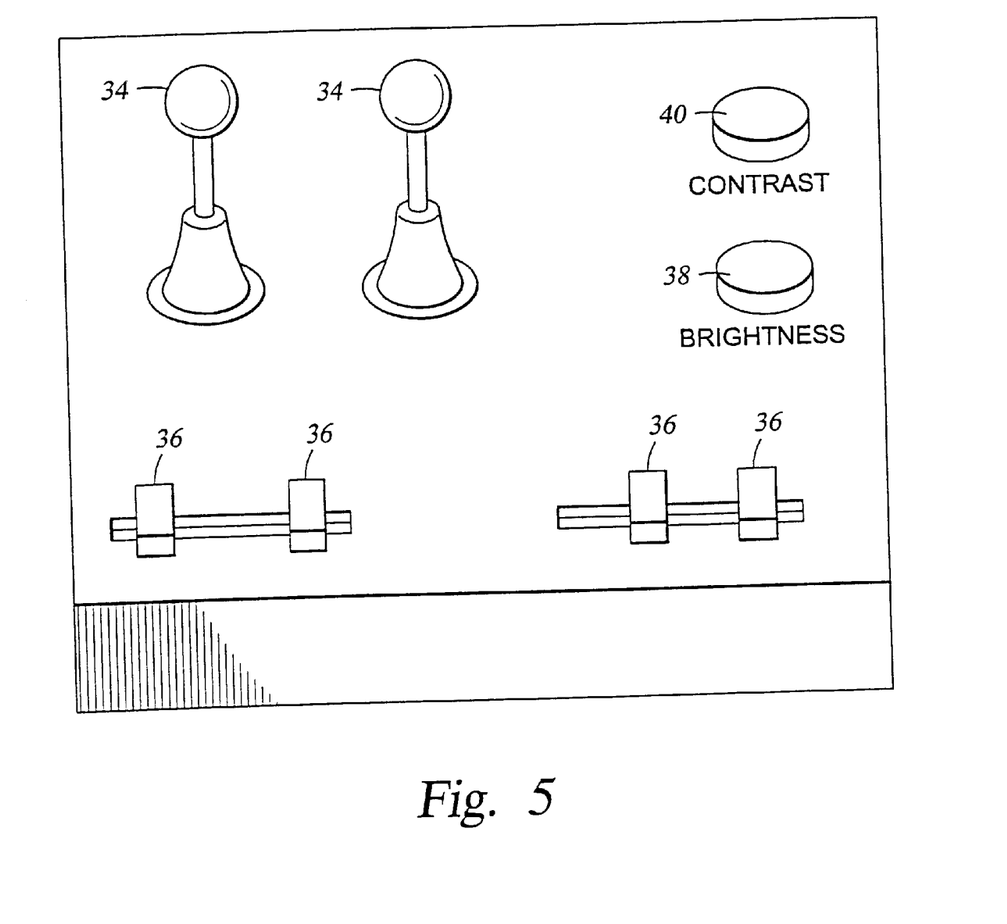
FIG. 5 is a schematic diagram of a control panel in accordance with an embodiment of the present invention.

A control panel for an embodiment of the present invention is shown in FIG. 5. Joysticks 34 are used to choose the orientation of one or more projections, and pairs of slide bars 36 choose the upper in lower limits of the depth of the projections, S. Brightness 38 and contrast 40 controls allow the user to adjust the display on one or more CRTs or other display devices. The present invention is not intended to be limited to any particular method of allowing a user to choose a projection orientation or control the displays. Although direction cosines are used in this disclosure to describe projection planes, it is not intended for a user to be restricted to inputting orientation information in that format.

In one embodiment of the present invention, the location of the catheter is superimposed on the image data after the projection(s) have been created. Generally, the creation of projections, P(u, v), from the image data file I(x, y, z) is a relatively slow process. Although it is understood that the trend towards faster and less expensive computer processing will ease this constraint. At the present time the projections are created less frequently than in real-time. This means that as the catheter moves, first superimposing the catheter location and I(x, y, z) and then creating one or more projections, P(u, v), may introduce a time-lag in displaying actual catheter location. Unlike the image data file I(x,y, z), which typically contains non-zero data samples at many thousands of locations corresponding to the entire volume of the imaged organs or tissues, the catheter location data will typically be relatively "sparse". That is, it will contain much fewer non-zero entries than I(x, y, z). An embodiment of the present invention exploits the fact that the catheter location data is relatively sparse compared to I(x, y, z), and superimposes the catheter location directly on the projection(s). In this way, the changing position of the catheter can be mapped onto the projection, without the need to re-create the projection from each data point within I(x, y, z). In most cases, the relatively sparse catheter location data can be directly superimposed on projections in much less time than is required to create the projection from I(x, y, z).

Figure 6:
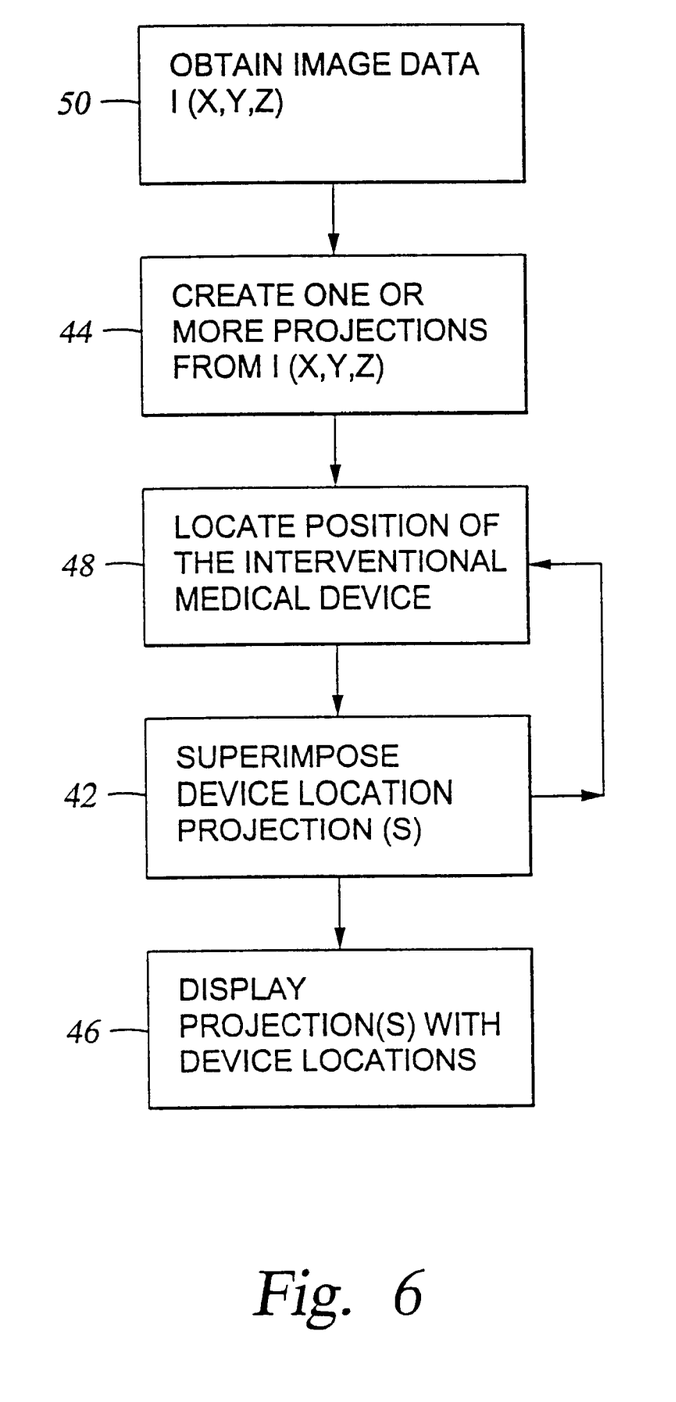
FIG. 6 is a flow chart of the imaging process in accordance with an embodiment of the present invention.

FIG. 6 shows a flow chart of an embodiment of the present invention where the intervention medical device location is superimposed 42 after the projection(s) are created 44, and then the projection with the device location is displayed 46. The process of locating the device position 48 is repeated frequently, preferably at a frequency close to the display monitor video refresh rate.

Re-starting the process, by obtaining updated image data 50, may be initiated by the user in situations such as where there is patient movement. With sufficient computer processing power, obtaining updated image data 50 may be repeated at predetermined frequency without user action.

The location of the catheter is preferably detected by the same ultrasonic imaging equipment that is used to create the image data, I(x, y, z), using the same global Cartesian coordinate system. By using an active catheter system, such as the vibrating mechanism of the '865 patent, the "catheter image" may be more easily detected, and distinguished from, the relatively passive surrounding environment. An embodiment of the present invention may also use one or more filters to further distinguish the active catheter image from background. Such filtering techniques are generally known to those of ordinary skill in the art.

The catheter image may take one of two preferred formats. First, it may match the format of the input file I(x, y, z) with only a relatively limited number of non-zero entries. For the catheter image this file will be called $I_c(x, y, z)$. In this format, $I_c(x, y, z)$ will contain the echodensity values of the catheter, corresponding to the actual 3-D image of the catheter, as seen by the ultrasound transducer. As discussed above, the $I_c(x, y, z)$ values may be the post-filter echodensity data.

Alternatively, the catheter image may correspond to one or more sets of Cartesian coordinates, representing the coordinates of one or more locations on the catheter in 3-D space. That is, the actual ultrasound image of the catheter is not used, only the coordinates of one or more points that may be used to determine the catheter location, and perhaps its orientation.

Using two points on a catheter to locate and orient the catheter in space is known in the art, as illustrated by FIG. 9 in the '853 patent. An embodiment of the present invention includes assignable attribute data field for each coordinate, along with the coordinates of the one or more locations on the catheter. Such a data field may store an intensity value corresponding to an amount of ultrasonic energy detected, for use in creating false color displays of the catheter image.

Regardless of the format of the catheter location data, the present invention performs a transformation of that location data into the coordinates of the projection(s). For catheter image files in the $I_c(x, y, z)$ format, this process may resemble (mathematically) the creation of $P(u, v)$ from $I(x, y, z)$, only with a much sparser input file. The projected catheter image(s) $P_c(u, v)$ can then be directly superimposed on the image data $P(u, v)$. This procedure is repeated, or performed as multiple parallel tasks, for each projection orientation.

For catheter location data stored as coordinate(s), or coordinate(s) and attribute data, only the individual coordinates need to be transformed into the coordinate systems of the projections. That is, there is no need to perform numerical integration on the larger number of data locations making up the catheter image. Such a transformation of one or more points to the coordinate system of the projections may be performed relatively quickly, in either software or hardware. The output of the transformation system may be two (planar) coordinates for each point location in a given projection, and the values of the associated attribute data. Mapping a location symbol to a CRT display at the location of these two coordinates is straight forward, and known to those of ordinary skill in the art. The attribute data may also be used in conjunction with the location symbol. For example, "cross-hairs", or an arrow symbol, could be mapped onto the CRT display of each projection at the current location of the catheter in that projection, with the color of the symbol correlated to the magnitude of vibration detected in a vibrating catheter.

An embodiment of the present invention converts catheter image data in the form of a $I_c(x, y, z)$ into one or more coordinates representing the catheter location in order to speed the data processing. The full ultrasound image of the catheter is sacrificed in such an embodiment, for the ease in processing data for only a few point locations. However, with one or two point locations, and the prior knowledge of the catheter geometry, there is no need to directly map the full catheter image to the display; all of the information can be carried by, or conveyed by, the symbols mapped directly to the monitors.

Unlike the projection data created from the image data $I(x, y, z)$, the superimposed catheter image does not require that the image intensities (gray scales) be accurately transformed unto the displays, only that the catheter locations be accurately transformed. It may be advantageous to modify the intensity of the catheter image, relative to the other image data, for display clarity. One embodiment of the present invention uses the catheter location as the center of projection depth when for creating the image for display.

Another embodiment of the present invention may use color image data files, where $I(x, y, z)$ is replaced by separate color space image files, such as $I_R(x, y, z)$, $I_G(x, y, z)$ and $I_B(x, y, z)$ corresponding to an image in RGB color space. Other color space formats may also be used, and the present invention is not intended to be limited to any particular color space representation. Given this disclosure, those of ordinary skill in the art will recognize how the present invention may be adapted to work with such color images.

Although various embodiments are specifically illustrated and described herein, it will be appreciated that modifications and variations of the present invention are covered by the above teachings and are with the purview of the appended claims, without departing from spirit and intended scope of the present invention. Moreover, the present invention may be implemented in software, firmware as well as in hardware, and in a broad range of computer architectures and is intended to be a general approach that includes a broad range of specific implementations.

What is claimed is:

1. An apparatus for displaying ultrasound volumetric object data and an interventional device on a two dimensional plane, comprising:
   a volumetric data file for storing a plurality of object intensity values, each of said intensity values mapped to a set of 3-D coordinates, wherein at least one set of said object intensity values obtained by direct measurement of said object during said interventional procedure is stored in said volumetric data file;
   a first projection plane for displaying a first projection of said object intensity values, whereby said first projection plane is defined by a first perpendicular vector;
   a first image projector for creating a first projection image on said first projection plane from said object intensity values projected along said first perpendicular vector;
   an interventional device locator for locating the interventional device at a device location mapped to said set of 3-D coordinates; and
   a first superimposer for superimposing said device location and said first projection image to create a first display image on a two dimensional plane.

2. An apparatus in accordance with claim 1, further comprising:
   a second projection plane for displaying a second projection of said object intensity values whereby said second projection plane is defined by a second perpendicular vector;
   a second image projector for creating a second projection image on said second projection plane from said object intensity values projected along said second perpendicular vector; and
   a second superimposer for superimposing said device location and said second projection image to create a second display image on a two dimensional plane.

3. An apparatus in accordance with claim 2, wherein:
   a preferred transformation defines an orientation relationship between said first perpendicular vector and said second perpendicular vector.

4. An apparatus in accordance with claim 2, wherein:
   said second display image is a view on a two dimensional plane useful to medical personnel performing a procedure.

5. An apparatus in accordance with claim 4, wherein:
   said second display image is a left anterior oblique (LAO) view of the object.

6. An apparatus in accordance with claim 4, wherein:
   said second display image is a RAO view of the object.

7. An apparatus in accordance with claim 2, further comprising:
   a second image range value for specifying a range of said object intensity values in said second display image.

8. An apparatus in accordance with claim 7, wherein:
   said second image range is centered on said interventional device location as measured along said second perpendicular vector.

9. An apparatus in accordance with claim 2, further comprising:
   a third projection plane for displaying a third projection of said object intensity values whereby said third projection plane is defined by a third perpendicular vector;
   a third image projector for creating a third projection image on said third projection plane from said object intensity values projected along said third perpendicular vector; and a third superimposer for superimposing said device location and said third projection image to create a third display image on a two dimensional plane.

10. An apparatus in accordance with claim 1, wherein:
said first display image is a view on a two dimensional plane useful to medical personnel performing a procedure.

11. An apparatus in accordance with claim 10, wherein:
said first display image is a right anterior oblique (RAO) view of the object.

12. An apparatus in accordance with claim 10, wherein:
said first display image is a LAO view of the object.

13. An apparatus in accordance with claim 1, further comprising:
a first image range value for specifying a range of said object intensity values in said first display image.

14. An apparatus in accordance with claim 13, wherein:
said first image range is centered on said interventional device location as measured along said first perpendicular vector.

15. An apparatus in accordance with claim 1, further comprising:
a first display image orientation control for defining said first perpendicular vector from a user input.

16. An apparatus in accordance with claim 1, wherein:
said superimposer updates said device location continuously.

17. An apparatus in accordance with claim 16, wherein:
said first image projector updates said object intensity values responsive to a user signal.

18. An apparatus in accordance with claim 16, wherein:
said first image projector updates said object intensity values in real-time.

19. An apparatus in accordance with claim 1, wherein:
the interventional device actively transmits a signal and said interventional device locator image generator is responsive to said signal.

20. An apparatus in accordance with claim 1, further comprising:
an output file generator for storing said first display image.

21. An apparatus for displaying ultrasound volumetric object data on a two dimensional plane and an interventional device, comprising:
a volumetric data file for storing a plurality of object intensity values, each of said intensity values mapped to a set of 4-D coordinates;
a first projection plane for displaying a first projection of said object intensity values, whereby said first projection plane is defined by a first perpendicular vector;
a first image projector for creating a first projection image on said first projection plane from said object intensity values projected along said first perpendicular vector;
an interventional device locator for locating the interventional device at a device location mapped to said set of 4-D coordinates; and
a first superimposer for superimposing said device location and said first projection image to create a first display image on a two dimensional plane.

22. An apparatus in accordance with claim 21, wherein:
said object intensity values are projected in the form of a cine loop.

23. An apparatus in accordance with claim 21, wherein:
said first display image corresponds to a single point in a repetitive sequence.

24. A method of displaying ultrasound volumetric object data and an interventional device on a two dimensional plane, comprising:
selecting a plurality of object intensity values mapped to a set of 3-D coordinates, wherein at least one set of said object intensity values is obtained by direct measurement of said object during an interventional procedure;
selecting a first projection plane for displaying a projection of said at least one set of object intensity values, whereby said first projection plane is defined by a first perpendicular vector;
projecting said at least one set of object intensity values along said first perpendicular vector onto a first two dimensional projection plane;
finding an interventional device location relative to said set of 3-D coordinates; and
superimposing said device location and said first two dimensional projection plane onto a first display image.

25. A method in accordance with claim 24, further comprising:
selecting a second projection plane for displaying a second projection of said object intensity values, projecting a second display, whereby said second projection plane is defined by a second perpendicular vector; and
projecting said plurality of object intensity values along said second perpendicular vector onto a second two dimensional projection plane; and
superimposing said device location and said second two dimensional projection plane onto a second display image.

26. A method in accordance with claim 25, wherein:
selecting a second projection plane is performed using said first perpendicular vector and a preferred transformation.

27. A method in accordance with claim 25, wherein:
said second projection plane conforms to a view useful to medical personnel performing a procedure.

28. A method in accordance with claim 27, wherein:
said second projection plane is a left anterior oblique (LAO) view.

29. A method in accordance with claim 27, wherein:
said second projection plane is a RAO view.

30. A method in accordance with claim 25, further comprising:
selecting a second image range value for limiting said plurality of said object intensity values which are projected on said two dimensional projection plane in said second display image.

31. A method in accordance with claim 30, further comprising:
centering said second display image on said device location, as measured along said second perpendicular vector.

32. A method in accordance with claim 25, further comprising:
selecting a third projection plane for displaying a third projection of said object intensity values, projecting a third display, whereby said third projection plane is defined by a third perpendicular vector; and
projecting said plurality of object intensity values along said third perpendicular vector onto a third two dimensional projection plane; and superimposing said device location and said third two dimensional projection plane onto a third display image.

33. A method in accordance with claim 24, wherein:

said first projection plane conforms to a view useful to medical personnel performing a procedure.

34. A method in accordance with claim 33, wherein:

said first projection plane is a right anterior oblique (RAO) view.

35. A method in accordance with claim 33, wherein:

said second projection plane is a LAO view.

36. A method in accordance with claim 24, further comprising:

selecting a first image range value for limiting said plurality of object intensity values which are projected on said two dimensional projection plane in said first display image.

37. A method in accordance with claim 36, further comprising:

centering said first display image on said device location, as measured along said first perpendicular vector.

38. A method in accordance with claim 24, further comprising:

repeating said finding of said device location continuously.

39. A method in accordance with claim 24, further comprising:

selecting a revised plurality of object intensity values in response to a user signal.

40. A method in accordance with claim 24, further comprising:

selecting a revised plurality of object intensity values continuously.

41. A method in accordance with claim 24, further comprising:

selecting a revised plurality of object intensity values in response to a motion greater than a threshold value.

42. A method of displaying ultrasound volumetric object data and an interventional device, comprising:

selecting a plurality of object intensity values mapped to a set of 4-D coordinates;

selecting a first projection plane for displaying a projection of said object intensity values, whereby said first projection plane is defined by a first perpendicular vector;

projecting said plurality of object intensity values along said first perpendicular vector onto said first projection plane;

finding an interventional device location relative to said set of 4-D coordinates; and superimposing said device location and said first projection plane onto a first display image.

43. A method in accordance with claim 42, wherein:

superimposing of said device location is performed upon images projected in the form of a cine loop.

44. A method in accordance with claim 42, wherein:

superimposing said device location is performed at a single point in a repetitive sequence.

* * * * *